United States Patent [19]
Gittleman

[11] Patent Number: 5,967,781
[45] Date of Patent: Oct. 19, 1999

[54] PROSTHODONTIC ABUTMENT APPARATUS AND METHOD

[75] Inventor: Neal B. Gittleman, Houston, Tex.

[73] Assignee: Implant Systems, Inc., Houston, Tex.

[21] Appl. No.: 09/105,645

[22] Filed: Jun. 26, 1998

[51] Int. Cl.[6] ................................................. A61L 13/12
[52] U.S. Cl. .......................... 433/172; 433/180; 433/214
[58] Field of Search ................................ 433/172, 173, 433/174, 175, 176, 180, 214, 141

[56] References Cited

U.S. PATENT DOCUMENTS

| | | | |
|---|---|---|---|
| 4,416,629 | 11/1983 | Mozsary et al. | 433/174 |
| 5,073,111 | 12/1991 | Daftary | 433/173 |
| 5,106,299 | 4/1992 | Ghalili | 433/172 |
| 5,527,182 | 6/1996 | Willoughby | 433/172 |
| 5,564,928 | 10/1996 | Gittleman | 433/180 |

FOREIGN PATENT DOCUMENTS

1008257A6  2/1996  Belgium .

OTHER PUBLICATIONS

Advanced Restorative Products Catalog (Sterngold ImplaMed®, Sunrise, Florida, 1997), pp. 39–55.
Advertisement: The ITI Dental Implant System (The Straumaun Company, Cambridge Mass.) from Summer 1993 *Implant Dentistry* (vol. 2, No. 2), p. 87.
Diameter Prosthetics Manual (Implant Innovations, Inc., Palm Beach Gardens, Florida, Mar., 1997).
Guidelines Narrow Platform brochure, Brånemark System® (Nobel Biocare AB, Sweden), 1997).
Guidelines Wide Platform brochure, Brånemark System® (Nobel Biocare AB, Sweden), 1997).
Gittleman, Neal B., "Windows for Telescopes and Implant Abutments," *Texas Dental Journal*, Apr. 1997 (pp. 10–16).
English, Charles E. "Root Intrusion in Tooth–Implant Combination Cases" *Implant Dentistry*, Summer 1993, vol. 2, No. 2 (pp. 79–85).
Gittleman, Neal B., "Retrieving Cemented Telescopic Prostheses: Technical Note," 5 *Implant Dentistry*, 1996 (pp. 91–92).
Lifecore Biomedical 1997–98 Oral Restorative Product Catalog (Lifecore Biomedical, Chaska, MN).
Prosthetic Catalog (Implant Innovations, Inc., Palm Beach Gardens, Florida, 1993).
Component Assembly flyer (Implant Innovations, Inc., Palm Beach Gardens, Florida, date uncertain but shows 1994 copyright date).

*Primary Examiner*—John J. Wilson
*Assistant Examiner*—Patrick A. Hilsmier
*Attorney, Agent, or Firm*—Mark R. Wisner

[57] ABSTRACT

A dental prosthodontic apparatus including an abutment which is implanted into the jaw of a patient and which is provided with a slot which accepts fitted risers of different lengths. The end of the riser is substantially flat and forms a shelf and the length of the riser is selected so that when the riser is inserted into the slot, the end is approximately level with the gum line of the patient. When a prostheses is mounted to the abutment, the proximal margin of the prosthesis forms a gap between the margin of the prosthesis and the shelf formed by the inserted riser. The gap provides opposed surfaces against which a prying instrument can be worked in the event the prosthesis needs to be removed from the abutment.

31 Claims, 5 Drawing Sheets

PROSTHODONTIC ABUTMENT APPARATUS AND METHOD

BACKGROUND OF THE INVENTION

The present invention relates to a dental prosthodontic apparatus and a method of securing and recovering a dental prosthesis. In more detail, the present invention relates to a dental prosthodontic apparatus which is provided with a gap for insertion of a prying instrument with surfaces formed in the gap against which the prying instrument bears for removing the prosthesis, the gap being formed by the lower margin of the prosthesis and the top surface of a riser which is fitted into the abutment on which the prosthesis is received, the fitted riser being sized so as to be slightly coronal to the patient's gum line.

Present dental practice tends toward the replacement of lost teeth with cylindrical or plate metal alloy abutments embedded in the bone of the mandible or maxilla to support the artificial tooth restoration. If extensive replacement of several teeth is needed, several abutments, alone or in conjunction with existing teeth prepared as abutments, are used to anchor the replacement prosthetic teeth.

In the last two decades, significant advances have occurred in both the abutments which are used for such replacements and in the methods used to implant the prosthodontic apparatus in the jaw. In one currently favored practice, titanium alloy abutment cylinders or plates are intimately installed in holes or slots drilled in the underlying bone of the jaw. Several months are allotted to allow the underlying bone to bond to the surfaces of the implant. For this reason, implant bodies are provided with at least one threaded hole on the crestal surface or edge. These holes are temporarily capped with a healing screw to prevent the invagination of soft tissue and/or bone into the internal threads. The soft tissue is sutured over the abutment until an intimate implant-bone bond is completed.

At the next surgical encounter, the soft tissue is resected and the healing screw is replaced with a metal alloy perimucosal extension of selectable height and emergence profile and the soft tissue is sutured around the base of this extension. This extension is usually bolted in place and prevented from rotating by locating pins and holes or internal and external matching hexagonal (or other regular polygonally-shaped) projections. These perimucosal extensions form the support for the artificial abutment(s) used to support the final prosthetic restoration.

The final prosthodontic restoration requires close mechanical mating between the abutment(s) and the internal aspect and underside of the prosthesis which is fitted on and cemented to the abutment. These closely matched parts often consist of telescoped, tapered conical surfaces requiring a tight, non-binding, "passive" fit on the abutment. This requirement demands inordinate precision from the laboratory technician and tests the technical skills of both the dentist and the laboratory technician. Parallel alignment of the axes of each abutment to prevent binding of the tapered fit is not easily achieved.

The methods and apparatus disclosed in Applicant's prior U.S. Pat. No. 5,564,928, in combination with an appropriate dental cement, yield a predictable, controllable technique for securing and, if necessary, retrieving the final restoration by providing a gap, or window, formed in the implant between the cemented prosthesis and abutment. The gap is formed of opposing surfaces on the prosthesis and the abutment with enough space between the surfaces to allow introduction of a prying instrument which can be manipulated to impose a force couple on the opposed surfaces. The dentist uses the prying instrument to apply even, measured force to gradually separate the prosthesis from the cement and gently remove it from the abutment.

Although the prosthodontic abutment described in Applicant's prior patent provides a satisfactory result, there is room for improvement. Specifically, because patients' gums are of varying thicknesses, the distance from the bone in which the abutment is implanted and the gum line varies from patient to patient and even in the same patient receiving multiple restorations. This variability creates a situation in which, even several sizes of the prosthodontic apparatus described in Applicant's Pat. No. 5,564,928 does not provide enough options to the restoring dentist to size the implant so that the gap between the prosthesis and the implant is positioned just coronal to the gum line. Even if several sizes of the prosthodontic apparatus described in that prior patent did provide enough variability, the mere fact that it must be provided in several sizes increases its cost and requires that the restoring dentist, lab or implant/abutment vendor keep a supply of parts of enough different sizes so as to provide the necessary variability.

It is, therefore, an object of the present invention to overcome this disadvantage by providing a dental prosthodontic apparatus which, even though provided in only several different sizes, is capable of being adapted for use in nearly every circumstance likely to be encountered by the restoring dentist or laboratory technician.

It is another object of the present invention to provide a dental prosthodontic apparatus with a gap between abutment and prosthesis the height of which can be changed relative to the patient's bone and soft tissue in which the abutment is sized to accommodate varying gum thicknesses.

It is another object of the present invention to provide a method of forming a gap in an implanted dental prosthodontic apparatus for allowing insertion of a prying instrument for retrieval of the prosthesis.

Yet another object of the present invention is to provide a method of mounting a dental prosthesis to an abutment connected to an implant placed in a jaw.

It is another object of the present invention to provide a dental prosthodontic kit having a plurality of risers of different heights for selection and insertion into a slot formed in an abutment so as to form a gap between the abutment having the riser of selected height therein and the prosthesis.

Other objects, and the advantages of the dental prosthesis of the present invention will be made clear to those skilled in the art by the following description of the presently preferred embodiments thereof.

SUMMARY OF THE INVENTION

The prosthodontic apparatus of the present invention achieves these objects by providing an elongate slot formed as part of an abutment with the longitudinal axis of the slot substantially parallel to the longitudinal axis of the abutment and on the lingual side of the abutment. The abutment is configured with a first portion comprising a substantially frustroconically tapered shaft and a second, central portion the surface of which is substantially flat and orthogonal to the longitudinal axis of the abutment and which forms the platform which the prosthetic restoration will contact. The abutment may be attached to the implant body by a compression screw directed through a shaft in the abutment and screwing into a threaded shaft in the implant body, which is a substantially cylindrical shaft and which is implanted into the bone of the maxilla or mandible. Alternatively, the implant body may be blade shaped.

The slot is configured to receive a riser which fits into and is retained in the slot. The risers are of various lengths and one end of the riser comprises a shelf which is substantially orthogonal to the longitudinal axis of the abutment-implant complex and preferably substantially parallel to the margin of the prosthesis mounted on the abutment when the riser is placed in the slot. The length of the riser is chosen so as to position the end comprising the shelf at a position which is just coronal to the gum line of the patient in which the prosthodontic apparatus is secured.

The present invention further teaches the formation of a groove in the surface of the abutment orthogonal to the longitudinal groove formed in the abutment connecting to the gap formed between the top of the riser and the margin of the prosthesis.

The present invention also teaches the provision of one or more holes for receiving means for gripping said fitted riser. In an alternative embodiment, the fitted riser is provided with an additional threaded shaft accepting a set screw to prevent dislodgement of said riser in a coronal direction. In the preferred embodiment, the gripping means is provided with prongs which fit into the holes and the restoring dentist uses the gripping means to insert and remove the fitted riser into/from the slot.

The present invention also teaches the use of a shield made of a material which is applied in liquid or paste form, subsequently hardens but which is easily removable from the surfaces of the abutment to which it is applied. The shield is used to fill the longitudinal groove in the abutment, the orthogonal groove, and the slot formed in the abutment prior to making an impression on the interior of the mold used to cast the prosthesis so that when the shield is removed and the positive cast of the prosthesis is fitted onto the abutment, the grooves and slot formed in the abutment will be free of excess material. In an alternative, the shield may be applied with the fitted riser in place in the slot so that the shield fills the grooves and the space forming the gap proximate to the shelf of the fitted riser.

A further teaching of the present invention is the method of securing a dental prosthesis on an abutment formed as part of an abutment-implant complex in a jaw comprising the steps of forming a shield in a first, longitudinal groove in an abutment, a second, orthogonal groove, and a slot formed the abutment and making an impression of the shielded abutment. The impression is then used to form a dental prosthesis and the shield is then removed from the slot and the grooves. A fitted riser is inserted into the slot and the prosthesis is applied to the abutment. The prosthesis is pressed onto the abutment while excess dental cement is extruded through the grooves until the top of the riser and the margin of the prosthesis form a gap into which a prying tool can be inserted for subsequent removal of the prosthesis.

The present invention further teaches the utilization of a dental prosthesis kit comprising a dental implant and abutment and a plurality of fitted risers of varying lengths, each riser being insertable into a slot formed in said abutment, and a tool formed to grip said fitted riser for insertion or removal from said slot.

BRIEF DESCRIPTION OF THE DRAWINGS

FIG. 7.1 is a perspective view of the dental prosthodontic apparatus of FIG. 3 showing a shield in place in the grooves and shelf formed in the abutment for casting an impression.

FIG. 7.2 is a perspective view of the dental prosthodontic apparatus of FIG. 3 showing a shield in place in the grooves and slot formed in the abutment for casting an impression.

FIGS. 12.1, 13, and 14 are side elevational views of three fitted risers, each of different heights, shown removed from the longitudinal slot of the dental prosthodontic apparatus of FIG. 3.

FIG. 12.2 shows a side elevational view of a fitted riser provided additionally with a threaded shaft to accept a set screw also shown ready for placement.

DETAILED DESCRIPTION OF THE PREFERRED EMBODIMENT

Figures 1, 2:
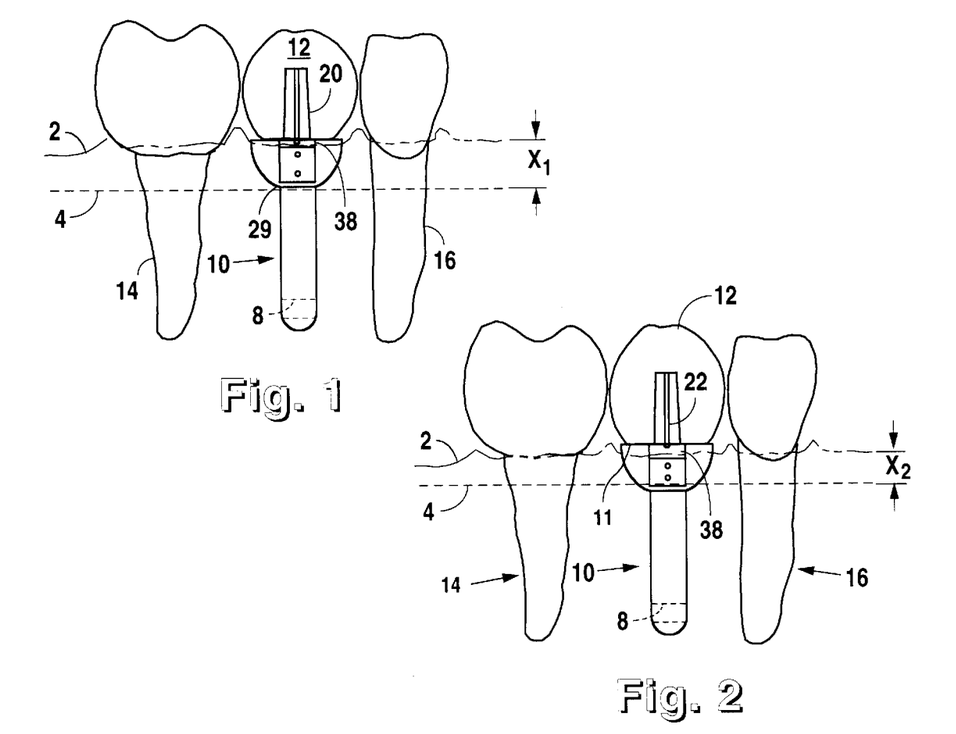
FIGS. 1 and 2 are partially schematic views of a preferred embodiment of the dental prosthodontic apparatus of the present invention from the lingual side as implanted in the jaw of a patient, the gum and bone lines being shown in phantom lines and of different relative dimensions.
Figure 3:
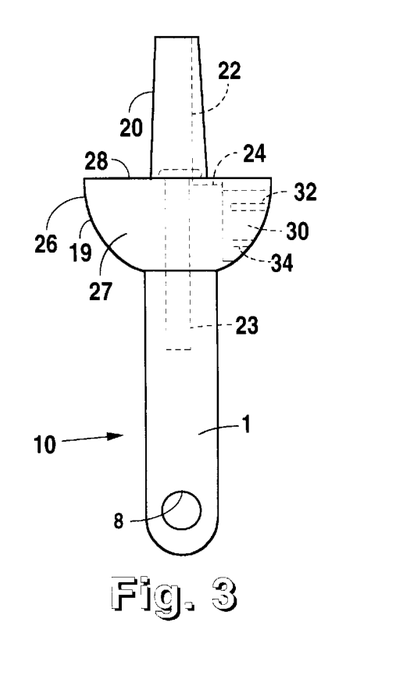
FIG. 3 is a side, elevational view of the dental prosthodontic apparatus of FIGS. 1 and 2 having the prosthesis removed therefrom for showing the grooves in the abutment and the fitted riser in the slot of the abutment.
Figure 4:
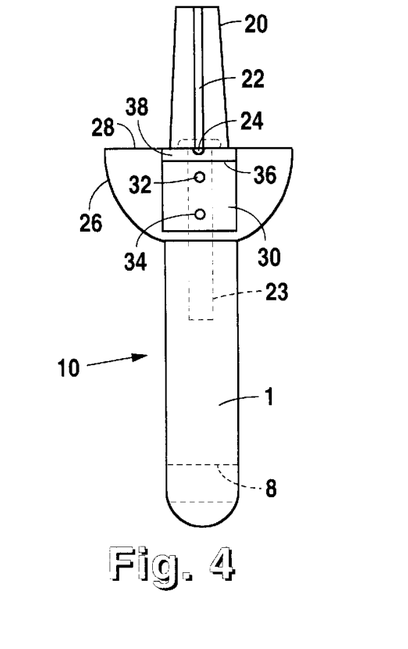
FIG. 4 is an elevational view of the lingual aspect of the dental prosthodontic apparatus of FIG. 3.
Figure 5:
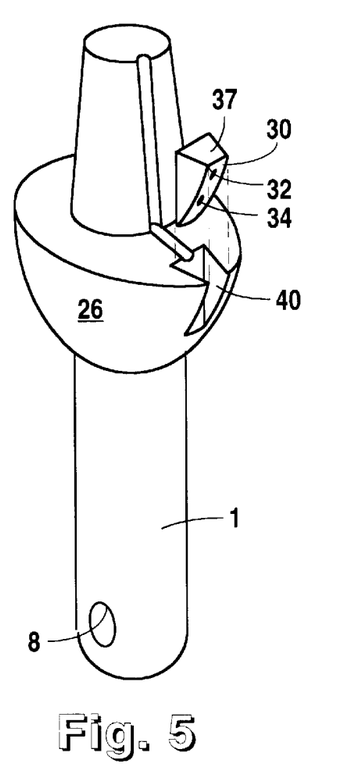
FIG. 5 is a perspective, partially exploded view of the dental prosthodontic apparatus of FIG. 3.
Figure 6:
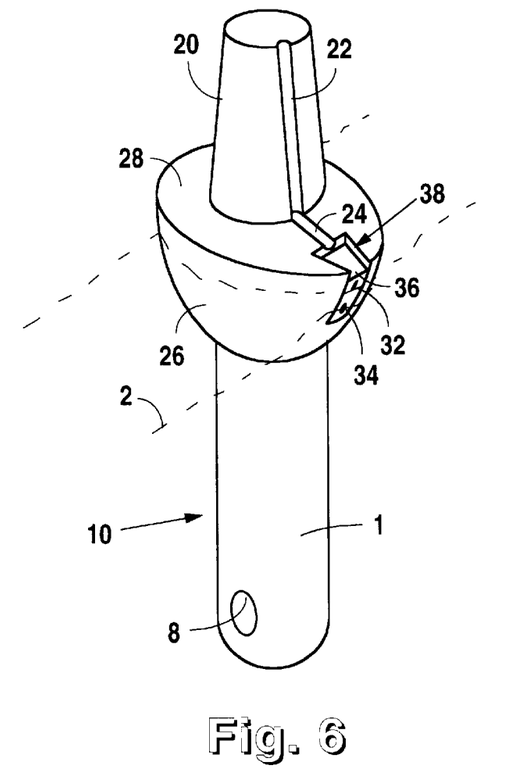
FIG. 6 is a perspective view of the dental prosthodontic apparatus of FIG. 3 showing a fitted riser in place in the longitudinal slot formed in the abutment and a phantom line representing the patient's gum line to illustrate the manner in which the shelf formed by the top surface of the fitted riser approximates the gum line.
Figure 8:
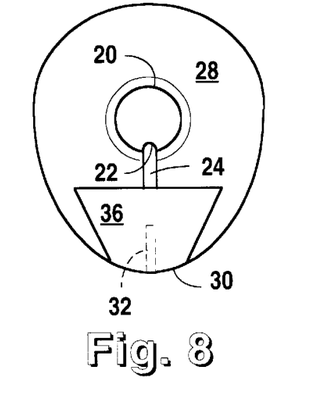
FIG. 8 is a top plan view of the dental prosthodontic apparatus of FIG. 3.
Figure 9:
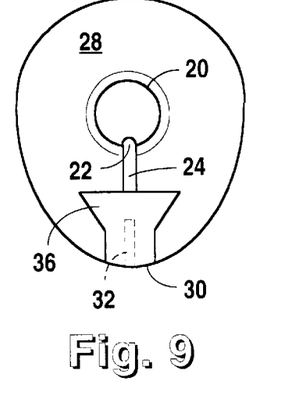
FIGS. 9, 10 and 11 show top plan views of three alternative embodiments of the dental prosthodontic apparatus of the present invention.
Figure 10:
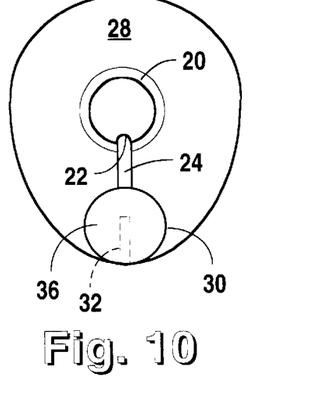
Figure 11:
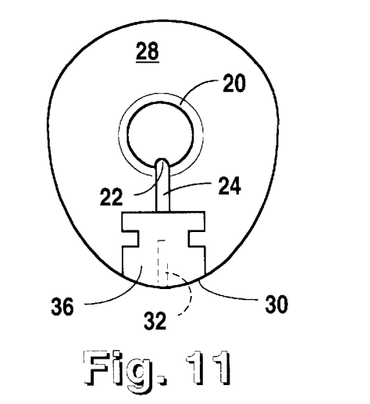

A preferred embodiment of the dental prosthodontic apparatus of the present invention is shown from the lingual aspect implanted in the jaw of a patient in FIGS. 1 and 2. The apparatus, indicated generally at reference numeral 10, is comprised of an elongate abutment 26 to which a prosthesis 12 is mounted and is implanted in the mandible or maxilla of the patient's jaw, the bone being represented by the dotted line B in the figures. FIGS. 1 and 2 further show the apparatus 10 situated between two normal teeth 14 and 16. The abutment 26 is formed with a transverse hole 8 which allows bony invagination when the abutment is implanted into the bone to add strength and stability. Although not shown well in FIGS. 1 and 2 because of the scale, the gap 38 formed between the proximal margin 11 of the prosthesis 12 and the shelf 37 comprised of the distal surface 36 of the fitted riser 30 (best shown in FIG. 5) receives a prying instrument (not shown) for removing the prosthesis 12 from abutment 26 as taught in prior U.S. Pat. No. 5,564,928, hereby incorporated into this disclosure in its entirety by this specific reference.

In the preferred embodiment, the abutment 26 is comprised of a first, preferably (although not necessarily) frustroconical portion 20, a second rounded portion 27 with a substantially flat surface 28, said flat surface 28 proximate to the first portion 20, the abutment 26 provided with a shaft accepting a compression screw 23. In the preferred embodiment, the compression screw 23 is inserted through the abutment 26 contacting and threadably inserted into the implant 1. In an alternative embodiment, the abutment 26 and the implant 1 are constructed as a unified piece. In a proper surgical implantation, the implant 1 is implanted into a hole (not numbered) in the bone of the maxilla or mandible and set deeply enough in the hole that the rounded surface 29 of the second portion 27 of abutment 26 rests on the surface 4 of the bone. As can be seen by comparison of FIGS. 1 and 2, the amount of tissue comprising the gum, the margin of which is represented by the line at 2, varies between the figures, as does the thickness of the gum tissue from patient to patient and even from location to location in the mouth of a single patient. The differences in the thickness of the gum tissue, represented by the dimensions $x_1$ in FIG. 1 and $x_2$ in FIG. 2, requires that the shelf 36 comprising one surface of the gap 38 into which a prying instrument is inserted for removing the prosthesis 12 from the implanted abutment 26 be at different heights so as to always be located above the gum line 2. In other words, the dimensions $x_1$ and $x_2$ representing the distance from the top surface 4 of the bone to the top surface 2 of the patient's gum also represent the distance along the longitudinal axis of abutment 26 between the shelf 36 and the rounded surface 29 of the abutment 26 which rests on the top surface of the bone 4.

If constructed in accordance with the above-incorporated patent, to obtain a proper fit of the abutment 26 in the patient's gum, the abutment 26 must be provided to the restoring dentist in a variety of sizes and/or relative proportions. To overcome the need for providing the abutment in such a wide variety of sizes and proportions, the abutment 26 of the prosthodontic apparatus of the present invention is provided with an elongate slot 22, best shown in FIGS. 3–6, in the second portion 27 thereof. Slot 40 is shaped to receive and affirmatively retain the fitted riser 30 therein so that, when the riser 30 rests therein, the distal surface 37 (this surface is referred to as a "distal," rather than a top, surface because when the prosthodontic apparatus 10 is implanted in the maxilla, the surface faces downwardly such that referring to a "top" surface is misleading, it being understood from this disclosure by those skilled in the art that the surface 37 is distal from the bone 4 of the patient's jaw) forms the shelf 36 which comprises one surface of the gap 38 into which a prying instrument is inserted for removing the prosthesis 12 from abutment 26.

Figure 13:
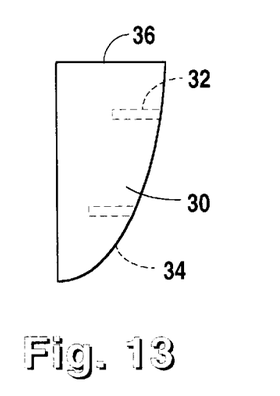
Figure 14:
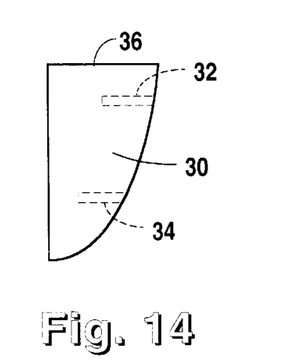

When the abutment of the prosthodontic apparatus of the present invention is constructed as shown in FIGS. 3–6, risers of different longitudinal dimensions as shown in FIGS. 12–14 are inserted by the restoring dentist into slot 40 to provide the proper spacing along the longitudinal axis of the abutment 26 so that the distal surface 36 of the riser 30 is located proximate the patient's gum line 2. Each of the risers shown in FIGS. 12–14 is provided with a plurality of holes 32 and 34 for receiving means for engaging the riser 30 top facilitate insertion and removal of the riser 30 in/from the longitudinal slot 40 in abutment 26. In the embodiment shown in FIG. 12.2, the fitted riser is additionally provided with a threaded shaft 33 penetrating through the fitted riser and into which may be inserted a set screw 35. In the embodiment shown in FIG. 18, the riser engaging means comprises a fork 52 with prongs 54 spaced so as to engage both of the holes 32 and 34 of riser 30. In the particularly preferred embodiment, the fork 52 is comprised of a resilient material such as plastic so that the prongs 54 and the axes of the holes 32 and 34 are not quite parallel so that the prongs 54 are deflected slightly upon insertion into the holes 32 and 34 so as to help provide a tight friction fit of the engaging means to the riser 30. However, because of the small size of the riser 30 and the tendency of the riser to be wetted by the oral mucosa, it is preferred that the riser engaging means be able to grip the riser 30 for removal from the slot 40.

Those skilled in the art who have the benefit of this disclosure will recognize that the fork 52 is but one form of riser engaging means which may be used to advantage. Other such engaging means may take the form of a clamp on the end of a handle, a fork with a single prong, a handle having a blade or point on the end for engaging a cleat or nipple formed on the lingual aspect of the riser, or a chisel which is simply driven into the abutment between the slot 40 and the riser 30 to pop the riser up out of the slot 40.

Figure 15:
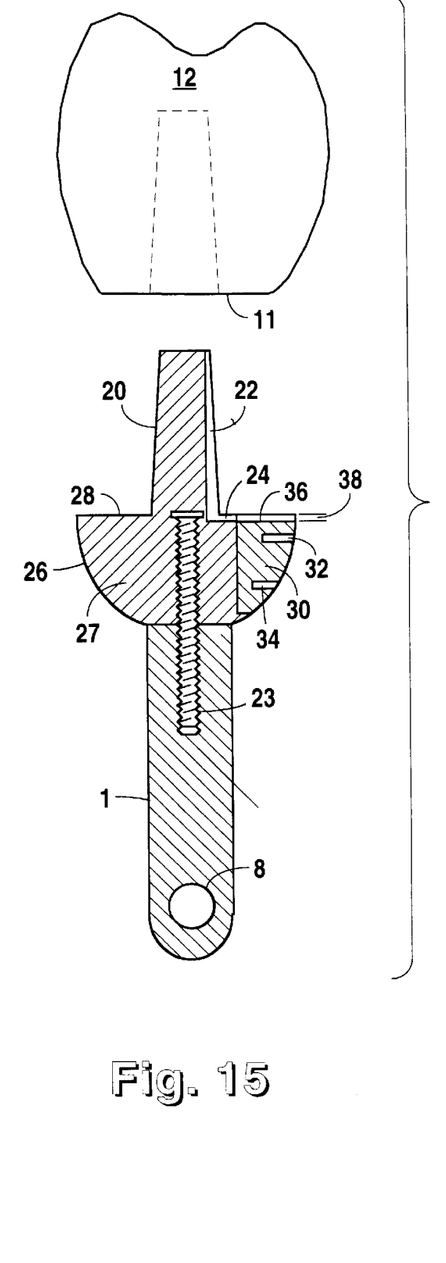
FIG. 15 is a longitudinal sectional, partially-exploded view (lingual aspect to the right) of a presently preferred embodiment of the dental prosthodontic apparatus of the present invention.
Figure 16:
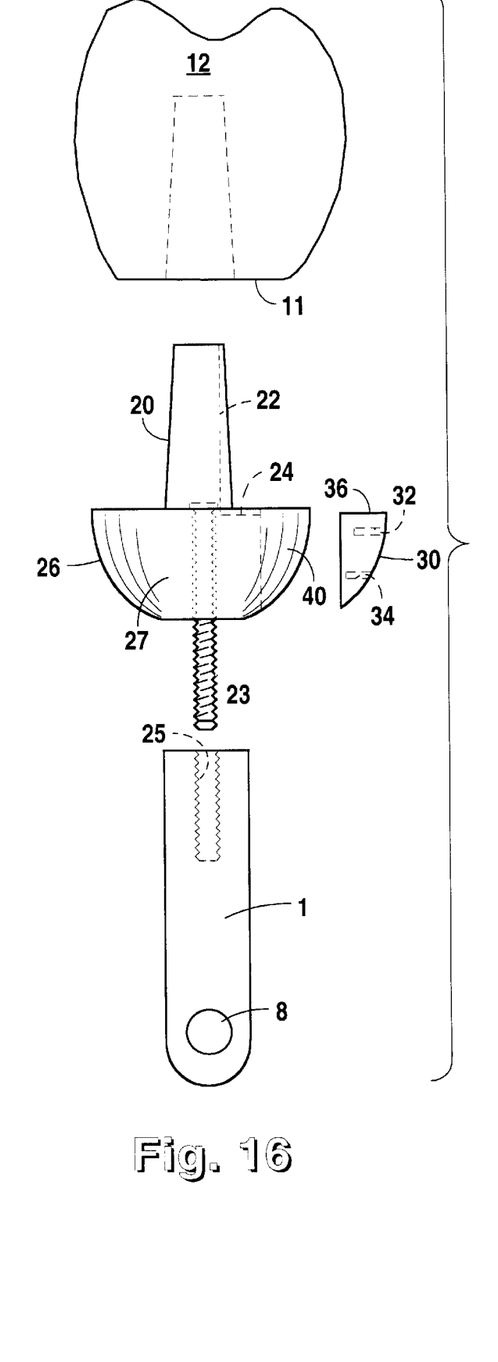
FIG. 16 is an exploded, side elevational view of the dental prosthodontic apparatus of FIG. 15.

FIGS. 15 and 16 show the prosthesis 12 positioned for fitting onto the first portion 20 of the abutment 26. In the embodiment shown, the third portion 23 of abutment 26 is comprised of a compression screw penetrating through the abutment 26 and threadable into the implant body 1 whereby the abutment 26 is secured to the implant body 1. In the alternative embodiment shown in FIG. 17, the abutment 26 and implant 1 are provided as a single, unified piece.

Referring once again to FIGS. 5–7, reference is made to the longitudinal groove 22 formed in the first portion of abutment 26. A second groove 24, perpendicular to groove 22 and substantially orthogonal to the longitudinal axis of abutment 26, is formed in the surface 28 of the second portion 27 of abutment 26 which connects to the longitudinal groove 22 and leads from groove 22 to the gap 38 that is formed between the proximal margin 11 of prosthesis 12 and the shelf 36 comprised of the distal surface 37 of fitted riser 30. The combination of the longitudinal and orthogonal grooves 22 and 24 functions in the same manner as the hydrostatic pressure relief channel described in Applicant's application Ser. No. 08/730,092, which is hereby incorporated into this disclosure in its entirety by this specific reference. Briefly, after an appropriate dental cement is applied to the prosthesis 12 and the prosthesis is then forced down over the first portion 20 of abutment 26, the excess cement is squeezed out from between the prosthesis 12 and abutment 26 through the channel formed by the grooves 22 and 24 into the gap 38. However, a difference between the apparatus described in Applicant's application Ser. No. 08/730,092 and the dental prosthodontic apparatus 10 of the present invention is that the fitted riser 30 of the apparatus 10 of the present invention is inserted into the slot 40 before the prosthesis 12 is pressed down over the first portion 20 of abutment 26.

Figure 71:
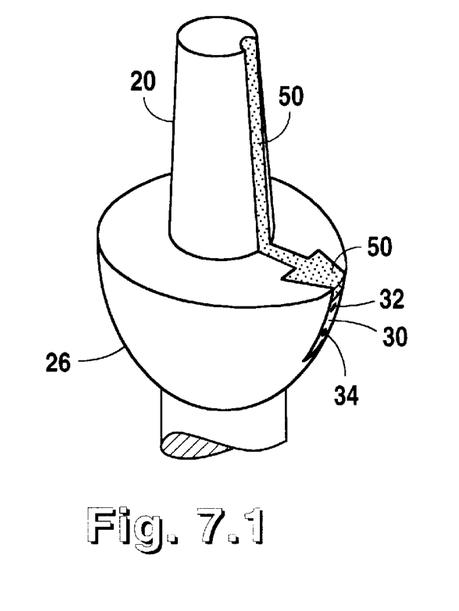
Figure 72:
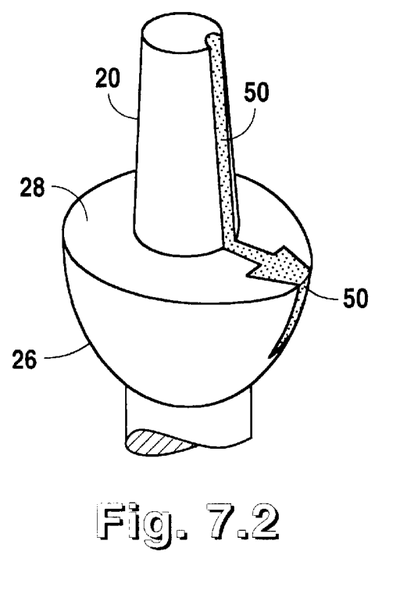
Figure 121:
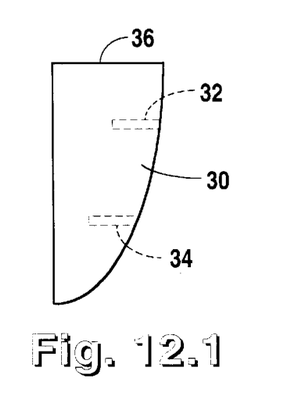
Figure 122:
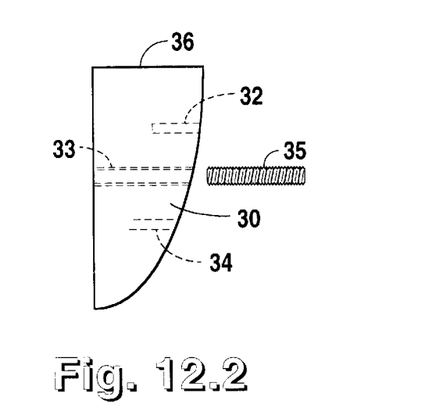

As noted above, to achieve the proper fit between the surgically implanted abutment 26 and the prosthesis, an impression must be made. FIG. 7.1 shows a shield 50 in place in grooves 22 and 24 and the gap 38 in abutment 26. FIG. 7.2 shows the shield 50 in place in grooves 22 and 24 and the slot 40 in abutment 26. The shield 50 is preferable comprised of a medical grade, moldable material which is cast in place in the implanted abutment 26 so as to fill the grooves 22 and 24 and the gap 38. Alternatively, the shield can also be used to fill the longitudinal slot 40 as shown in FIG. 7.2. In a presently preferred embodiment, this material is a curable silicone material such as SILASTIC® (Dow Corning) silicone polymer which is mixed with a curative while it is squeezed from a tube in a manner known in the art into the grooves 22 and 24 and gap 38. Polymers such as SILASTIC® have the advantage of being easily trimmed so as to remove excess polymer and then, once the impression has been taken, easily removed from the abutment.

Figure 17:
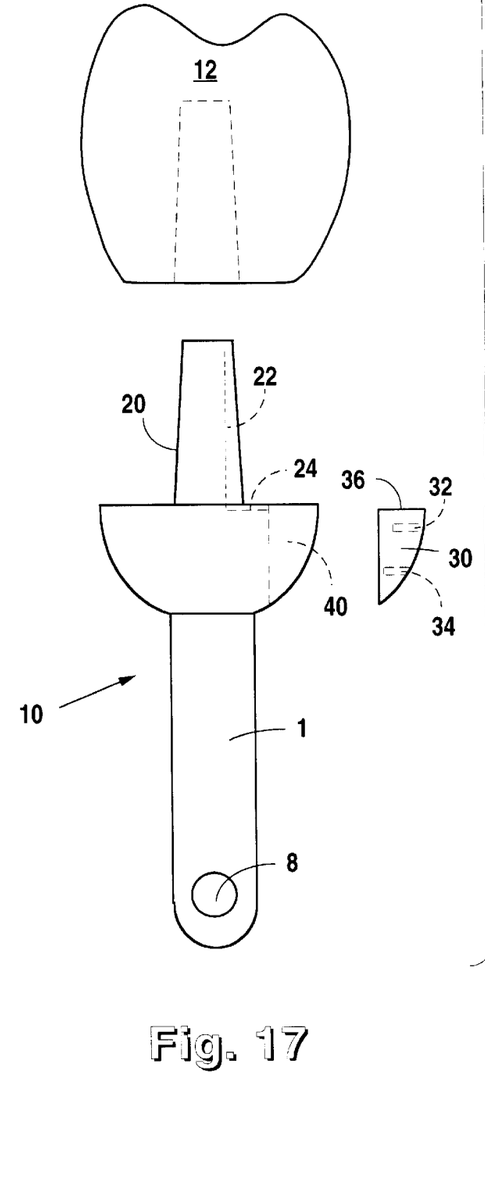
FIG. 17 is an exploded, side elevational view of another alternative embodiment of the dental prosthodontic apparatus of the present invention.

FIG. 17 shows the abutment-implant complex 10 as a unified construct rather than two threadably connected pieces.

Figure 18:
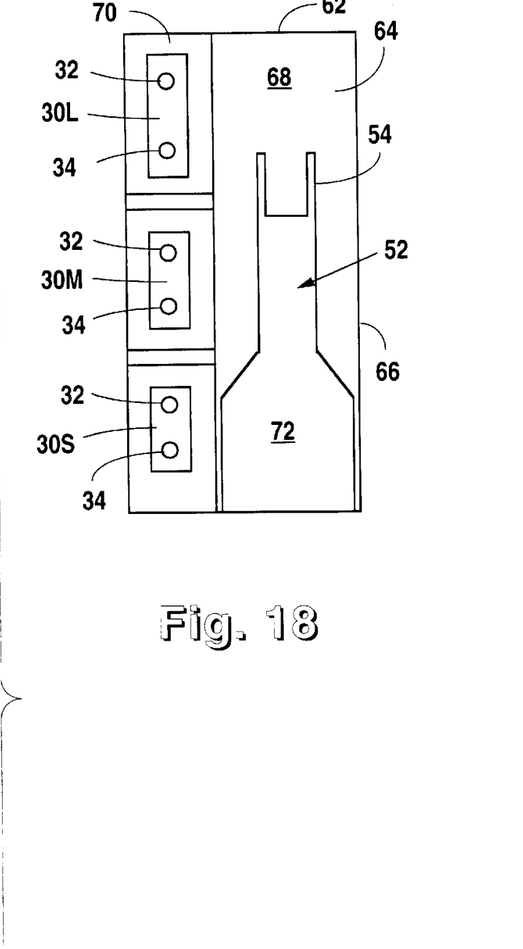
FIG. 18 is a top plan view of a preferred embodiment of a kit constructed in accordance with the teachings of the present invention including a plurality of fitted risers and means for engaging the risers.

Referring now to FIG. 18, there is shown a kit which is provided in accordance with the teachings of the present invention. In the preferred embodiment, the kit, indicated generally at reference numeral 60, is comprised of a vacuum-formed plastic tray 62 to which a sterile film 64 can be heat or otherwise bonded as known in the art so that the tray and its contents are sterile around the outer periphery 66 thereof. The tray 62 is formed into a plurality of compartments 68, some 70 of which are sized and shaped so as to provide an exact fit for different size risers 30s, 30m, and 30l, which are contained therein. Because the risers 30s, 30m, and 30l, as a result of their shape and relatively small size, sometimes have a tendency to be a bit elusive, the compartments 70 formed in tray 62 serve the function of restraining the risers 30s, 30m, and 30l from movement when the restoring dentist is using the riser engaging means to handle the riser.

One of the compartments in tray 62 provides an elongate handle 72 having prongs 54 formed on the end thereof of the type described above to provide a fork 52 for engaging the complementary holes 32 and 34 on the risers 30s, 30m, and 30l. Because the tray 62, in its preferred embodiment, is comprised of plastic, when it is desired to utilize the fork 52 for handling the risers, fork 52, which is molded from the same plastic and integrally with the tray 62, is broken off from its compartment in the tray 62 for use in the manner described above.

From the foregoing it is apparent that the present invention is well adapted to attain the properties and features set forth. While several preferred embodiments of the present invention have been shown and described, various modifications and changes may be made to those embodiments without departing from the true spirit and scope of the invention. It will be understood from this disclosure by persons skilled in the art that the apparatus and methods illustrated and described hereinabove are given by way of example only and may be varied widely within the scope of the appended claims.

What is claimed is:

1. A dental apparatus having a prosthesis mounted thereto, said prosthesis removable with a prying instrument, comprising:
   a prosthesis;
   an abutment to which said prosthesis is mounted having a slot formed therein; and
   a fitted riser having a surface comprising a shelf received within the slot in said abutment, the shelf of said fitted riser and the margin of said prosthesis forming a gap for receiving a prying instrument therein.

2. The apparatus of claim 1 wherein said fitted riser is provided in a plurality of longitudinal dimensions.

3. The apparatus of claim 1 wherein the longitudinal dimension of said fitted riser length is less than the length of the slot in said abutment.

4. The apparatus of claim 1 wherein said fitted riser is provided with a hole for receiving means for engaging said fitted riser.

5. The apparatus of claim 4 additionally comprising a fitted riser, said riser engaging means comprising a fork having a prong formed thereon which is received within the hole in said fitted riser.

6. The apparatus of claim 5 wherein said fitted riser is provided with a plurality of holes and said fork is provided with a plurality of prongs for receiving within the holes.

7. The apparatus of claim 6 wherein the longitudinal axes of the holes in said fitted riser are not parallel.

8. The apparatus of claim 1 wherein said abutment is provided with a first groove substantially parallel to the longitudinal axis of said abutment.

9. The apparatus of claim 8 wherein said abutment is provided with a second groove substantially orthogonal to said first groove and connecting said first groove and the gap.

10. The apparatus of claim 9 additionally comprising a shield for said first and second grooves.

11. The apparatus of claim 10 wherein said shield also shields the gap.

12. The apparatus of claim 10 wherein said shield also shields the slot.

13. The abutment of claim 1 wherein the slot in said abutment is formed with shape which resists movement of said fitted riser in a direction substantially orthogonal to the longitudinal axis of said abutment.

14. A method of forming a gap in a dental abutment comprising the steps of:
   affixing said abutment to an implant in the jaw;
   inserting a fitted riser into a slot formed in said abutment to form a shelf; and
   placing a prosthesis on said abutment proximate to said fitted riser to form a gapped space therebetween, the shelf and said prosthesis defining surfaces against which a prying instrument can be applied.

15. The method of claim 14 wherein one of a plurality of fitted risers of different lengths is inserted into the slot in said abutment with said fitted riser closely proximating the lingual gum line adjoining said abutment.

16. The method of claim 14 wherein said fitted riser is inserted into and/or removed from the slot in said abutment using means for engaging said fitted riser.

17. The method of claim 14 wherein excess dental cement applied to said prosthesis is extruded through a groove formed in said abutment into the zapped space.

18. The method of claim 17 additionally comprising shielding the groove and making an impression of the shielded abutment.

19. A method of mounting a dental prosthesis on an abutment implanted in the jaw of a patient comprising the steps of:
   a. inserting a shield into a groove and a slot formed in an abutment implanted in the jaw of a patient;
   b. making an impression of the shielded abutment;
   c. removing the shield from the groove and the slot;
   d. inserting a fitted riser into the slot;
   e. applying dental cement to a prosthesis; and
   f. applying the prosthesis to the abutment to closely approximate the prosthesis to the fitted riser and extrude excess cement through the groove and a gap formed between the prosthesis and the riser.

20. A kit for use in connection with a dental prosthodontic apparatus, the dental prosthodontic apparatus comprising an abutment implanted in the jaw of a patient and comprising a longitudinal slot, the kit comprising:

a plurality of fitted risers of different lengths for insertion into the slot formed in said abutment, means for engaging a fitted riser to facilitate insertion or removal from said slot; and a container for said fitted risers and said riser engaging means.

21. The kit of claim 20 wherein said container comprises a sterile package.

22. The kit of claim 20 wherein said container further comprises a plurality of compartments shaped and sized to contain the different lengths of fitted risers.

23. The kit of claim 20 wherein said riser engaging means is formed integrally with said container for detachment therefrom.

24. A dental abutment comprising:

a first portion comprising a shaft having a groove formed thereon, the groove being substantially parallel to the longitudinal axis of the shaft;

a second, central portion integral with said first portion and having a slot formed on the external surface thereof running substantially parallel to the longitudinal axis of said second portion; and a third portion extending from said second portion in a direction substantially opposite said first portion wherein said third portion is implantable in the jaw of a patient.

25. The dental abutment of claim 24 additionally comprising a fitted riser received within the slot formed in said second portion.

26. The dental abutment of claim 25 wherein the slot formed in said second portion is shaped to retain said fitted riser therein.

27. The dental abutment of claim 25 wherein said second portion is provided with a substantially flat surface proximate said first portion.

28. The dental abutment of claim 27 wherein the slot formed in said second portion opens to the flat surface for receiving said fitted riser.

29. The dental abutment of claim 28 wherein the surface of said fitted riser and the flat surface are at different heights.

30. The dental abutment of claim 24 additionally comprising a compression screw for securing said third portion to said second portion.

31. The dental abutment of claim 24 wherein the groove in said first portion connects to the slot in said second portion.

* * * * *